United States Patent
Armijo Torres et al.

(10) Patent No.: US 8,855,852 B2
(45) Date of Patent: Oct. 7, 2014

(54) METHOD AND SYSTEM FOR MONITORING A STRUCTURE

(71) Applicant: EADS Construcciones Aeronauticas, S.A., Sociedad Unipersonal, Madrid (ES)

(72) Inventors: José Ignacio Armijo Torres, Madrid (ES); Javier Gómez-Escalonilla Martín, Madrid (ES); Jaime García Alonso, Madrid (ES)

(73) Assignee: EADS Construcciones Aeronauticas, S.A., Sociedad Unipersonal, Madrid (ES)

( * ) Notice: Subject to any disclaimer, the term of this patent is extended or adjusted under 35 U.S.C. 154(b) by 0 days.

(21) Appl. No.: 13/782,622

(22) Filed: Mar. 1, 2013

(65) Prior Publication Data

US 2013/0245879 A1    Sep. 19, 2013

(30) Foreign Application Priority Data

Mar. 5, 2012  (EP) .................................... 12382082

(51) Int. Cl.
*G01N 19/08* (2006.01)
*G01M 5/00* (2006.01)

(52) U.S. Cl.
CPC ............ *G01N 19/08* (2013.01); *G01M 5/0016* (2013.01); *Y02B 10/30* (2013.01); *G01M 5/0008* (2013.01)
USPC .............................. 701/31.9; 702/34; 714/39

(58) Field of Classification Search
None
See application file for complete search history.

(56) References Cited

U.S. PATENT DOCUMENTS

| | | | | |
|---|---|---|---|---|
| 6,480,792 | B1 * | 11/2002 | Prendergast | 702/42 |
| 7,328,625 | B2 * | 2/2008 | Sundermeyer et al. | 73/806 |
| 2006/0004499 | A1 * | 1/2006 | Trego et al. | 701/29 |
| 2008/0114531 | A1 * | 5/2008 | Kagawa | 701/119 |

FOREIGN PATENT DOCUMENTS

WO    WO 00/25272    5/2000

OTHER PUBLICATIONS

Etzkorn, Ben, Nov. 15, 2011, Data Normalization and Standardization, BE Blog—Finance Thoughts.*
Wattenberg, Frank, Dec. 28, 2003, Mathematical Structure—Vector Spaces Magnitude or Length, Montana State University.*
European Patent Application No. 12382082.1 dated Mar. 5, 2012.

* cited by examiner

*Primary Examiner* — Helal A Algahaim
*Assistant Examiner* — Kelly E Darby
(74) *Attorney, Agent, or Firm* — Jenkins, Wilson, Taylor & Hunt, P.A.

(57) ABSTRACT

A method and system of monitoring a structure, the method including: a) synchronously acquiring data comprising a plurality of operational parameters and at least one strain data, b) building a significant points dataset from the data acquired in step a), and c) modelling a relationship between the operational parameters and the strain data using the built significant points dataset to train a non-adaptive prediction functional supervised approximation method, wherein the step of building a significant points dataset comprises deletion of redundant information from the acquired data. The resultant models may be used to process structure real operation data in order to estimate the eventual crack initiation and crack growth on a set of predefined locations of the structure.

15 Claims, 8 Drawing Sheets

METHOD AND SYSTEM FOR MONITORING A STRUCTURE

TECHNICAL FIELD OF THE INVENTION

Cross-Reference to Related Applications

This application claims the benefit of the filing date of European Application Serial No. EP12382082.1 filed Mar. 5, 2012 the disclosure of which is hereby incorporated herein by reference.

The present invention relates to a method and system for monitoring a structure, in particular related to prognosis of fatigue and damage tolerance. The present invention is applicable to any plant structure, wind turbine, ship, building, bridge, tower and preferably but not necessarily to an aircraft.

BACKGROUND OF THE INVENTION

Structural fatigue can be defined as the failure of a material due to the progressive growth of minute cracks under cyclic loading. The fatigue life of a plant structure is, in general words, the time to failure under a particular cyclic loading environment. The evaluation of the fatigue life consumption is an important part of plants design and calculation, but should be also controlled during the plant's operational life, by means of a so-called Structural Fatigue Monitoring System.

A plethora of monitoring systems has been conceived to evaluate the fatigue life consumption of aircraft structures. They have been used traditionally in military aviation and more recently in certain applications of civil aviation. There are two main advantages of this kind of systems: to ensure the safe operation of the aircraft and to reduce the costs of ownership by optimizing aircraft usage and maintenance tasks during the whole operational life.

Most of the fatigue monitoring systems include some characteristics that allow classifying them into groups according to following three main features: system philosophy, technique basis and concept of application.

The philosophy defines the scope of the system. The fatigue monitoring systems can be divided into two groups according to their philosophy, damage detection and damage prognosis. The aim of the systems under the damage detection group is to locate and measure the position and severity of the eventual damages (coming from structural fatigue or from any other source like corrosion, accidental, etc.). On the other side, the systems belonging to the damage prognosis category estimate the position and/or severity of the possible damages selected from a predefined set and considering a particular aircraft usage.

The technique basis determines what kind of variables are going to be used by the system in order to either detect or forecast the damage. Two main groups can be identified: direct techniques and parametric techniques. The direct systems measure directly in the structure some physical variables that can be used without the aid of an external model. This is an inductive technique because the system makes global assumptions from a set of particular data. For example, the system can include a number of strain sensors to measure the strains at some locations of the structure, and use that information to perform fatigue and damage tolerance calculations. The parametric systems use global operational parameters of the aircraft to feed a particular model and obtain the necessary data. This is a deductive technique because it makes particular assumptions about the structure based on general measurements. For example, flight cycles and flight hours may be used to control aircraft usage and apply the maintenance program according to a set of aircraft sortie profile codes.

Both techniques have advantages and disadvantages. Direct systems are accurate and precise because the variables used for the location (damage detection systems) or crack initiation and crack growth calculations (damage prognosis systems) are directly measured from the structure, but the installation and maintenance cost of the sensors is usually high. On the other hand, parametric systems are, in general, less accurate and precise due to the need of using an external model to obtain useful data (actually, nowadays the main challenge to obtain a reliable parametric system is the complexity of developing an accurate model to process the information), but they are less expensive than the former as in many cases the data come from other systems already installed in the aircraft.

Historically, parametric systems were developed earlier than direct systems due to their simplicity (e.g., vertical load factor exceedances counters). Once the technology evolved, increasingly sophisticated recorders began to be installed on-board (e.g., strain data recorders), and direct systems began to be used, being the preferred concept for years. During the last two decades parametric systems have been used again due to the improvement in the models that process parametric data and in the computation capabilities.

Finally, there are three application concepts depending on the number of aircraft that are monitored and the period of time during which they are tracked:
  Individual Aircraft Tracking (IAT), where every aircraft of the fleet is monitored during its whole operational life;
  Temporary Aircraft Tracking (TAT) when a limited number of aircraft are monitored during a limited period of time; and
  Selected Aircraft Tracking (SAT) when some aircraft of the fleet are monitored during its whole operational life.

The current invention presents a prognosis parametric method and system that allows individual aircraft tracking, joining the precision and accuracy of prognosis direct systems and the low cost of previous prognosis parametric systems. The present invention is applicable not only to aircraft, but to any plant structure, such as wind turbines, ships, buildings, bridges or towers, in which global parametric data can be associated to a level of strain in one or several locations of the structure.

SUMMARY OF THE INVENTION

The aforementioned drawbacks are solved by means of a method according to claim 1 and a system according to claim 14. The dependent claims define preferred embodiments of the invention.

The method of monitoring a structure according to the invention, comprises the following steps:
a) acquiring data, the data comprising a plurality of operational parameters $x_i(t_j)$ and at least one strain data $y(t_j)$, the operational parameters $x_i$ and the strain data y being acquired synchronously over a time series basis $(t_1, t_2, \ldots, t_m)$ using the same or different sampling rates;
b) building a significant points dataset from the data acquired in step a); and
c) modelling a relationship between the operational parameters $x_i(t_j)$ and the strain data $y(t_j)$ using the built significant points dataset to fit a non-adaptive prediction functional supervised approximation method,
wherein the step of building a significant points dataset comprises:

(b1) for each time sample $t_j$, j=1, ..., m, determining the data modulus $\|\bar{\mu}(t_j)\|$ of data vectors $\bar{\mu}(t_j)$ defined as:

$$\bar{\mu}(t_j) = (x_1(t_j), x_2(t_j), \ldots, x_n(t_j); y(t_j)),$$

the data modulus $\|\bar{\mu}(t_j)\|$ being calculated as:

$$\|\bar{\mu}(t_j)\| = \sqrt{\sum_{i=1}^{n} \tilde{x}_i(t_j)^2 + \tilde{y}(t_j)^2}$$

with $$\tilde{x}_i(t_j) = 2 \cdot \frac{x_i(t_j) - x_i^{min}}{x_i^{max} - x_i^{min}} - 1, \text{ for } i = 1, \ldots, n;$$

$$\tilde{y}(t_j) = 2 \cdot \frac{y(t_j) - y^{min}}{x^{max} - x^{min}} - 1$$

and $x_i^{min}$, $x_i^{max}$, $y^{min}$, $y^{max}$ being respectively the minimum and maximum values for $x_i$ and the minimum and maximum values for y in the time series $(t_1, t_2, \ldots, t_m)$;
(b2) sorting the data vectors $\bar{\mu}(t_j)$, j=1, ..., m, in $N_R$ groups according to the value of their modulus, each group including data with values of modulus within a defined range;
(b3) computing within each group the angle α between pairs of vectors and when the angle between a first vector and a second vector is less than or equal to a predetermined angle θ, deleting one of the two vectors.

The strain data $y(t_j)$ may be obtained from one or several structural locations of the structure.

In a preferred embodiment of the method, the non-adaptive prediction functional supervised approximation method is performed by an ANN (Artificial Neural Networks), although other methods such as Space State Models, polynomials or Autoregressive Models may be used.

In an embodiment of the method, the data vectors $\bar{\mu}(t_j)$ having maximum and minimum strain values are retained in each group in step (b3).

In an embodiment of the method, a minimum number of group points is associated to each group, so that when the number of significant points retained in a group after step (b3) is below the minimum number, the group is split into two sub-groups of equal size and step (b3) is repeated for each of the sub-groups until the minimum number of significant points is retained in the original group.

In an embodiment of the method, the acquired data $(x_i, y)$ are pre-processed prior to the step of building the significant points dataset, the step of pre-processing the acquired data preferably including at least one selected from: application of an error detection and correction algorithm, normalization, filtering, re-sampling and generating a low frequency dataset. In a preferred embodiment, the step of pre-processing the acquired data $(x_i, y)$ comprises generating a low frequency dataset and the significant points dataset are built from the low frequency dataset.

The method may include a step of validating the modelled relationship between the operational parameters $x_i(t_j)$ and the strain data $y(t_j)$ using the acquired data which are not included in the significant points dataset and optionally points taken from the significant points dataset. In this embodiment, the method preferably comprises feeding the trained and validated modelled relationship with the original, not-reduced, low frequency dataset, and computing adjustment factors as the ratio between the model output obtained in the previous step, i.e. the low frequency calculated strain, and the full bandwidth strain.

In an embodiment the method comprises a step of computing a strain history of at least one structure based on the trained and validated model, the acquired operational parameters and the computed adjustment factors. The method may include an additional step of pre-processing the acquired parameters.

In an embodiment, the method comprises a step of correction of fatigue life based on computed strains using the adjustment factors.

In an embodiment, the acquired parameters are pre-processed to produce the original bandwidth strain, and the method further comprises checking the in-service continuous system performance, by comparing the fatigue life based on the full bandwidth strain with the life based on computed strain. The method may comprise applying a corrective task in the case of a bad result in the checked in-service continuous system performance. The corrective task may comprise updating the modelled relationship and/or updating the significant points dataset.

In an embodiment, the method comprises using the computed strains to calculate the fatigue life consumption and/or damage tolerance of a set of locations of the structure.

The acquired data and/or the computed outputs may be stored in a database.

In a preferred embodiment, the method is applied to at least one aircraft structure, the operational parameters $x_i(t_j)$ being obtained from a number N of aircraft and the strain data $y(t_j)$ being obtained from a number M of reference aircraft, M being less or equal than N. Preferably, M is substantially 10-20% of N. The strain data $y(t_j)$ may be obtained from one structural location of each reference aircraft, but preferably strain data $y(t_j)$ is obtained from more than one structural location of each reference aircraft.

In a second inventive aspect, the invention defines a system for monitoring a structure comprising: an acquisition and recording device adapted to collect operational parameters from at least one structure, at least one physical strain sensor installed in a selected location of the structure, and processing means adapted to perform the steps of the method according to the first inventive aspect.

In a preferred embodiment, the structure to be monitored is at least one aircraft. In this case, the acquisition and recording device is preferably an on-board device connected with aircraft computers and/or dedicated sensors to collect aircraft operational parameters from the aircraft and strain signals from at least one physical strain sensor if installed in a reference aircraft. The processing means may be implemented in a ground processing facility.

The method and system of the invention can be understood as a set of virtual strain sensors constructed with a non-adaptive prediction functional supervised approximation method, such as an ANN, and allows generation of stress time series that can be used to perform crack initiation and crack growth estimations on a set of predefined locations of a structure. More specifically, the invention refers to a method and system that allow obtaining a set of virtual strain sensors, which compute the strains in selected points of the plant structure from its usual operation data. The method and system of the invention allow the estimation of the moment of crack initiation and the subsequent crack growth rates in certain predefined locations of the structure thus providing additional means to complement the maintenance program of the structure taking into account its real operation.

All the features described in this specification (including the claims, description and drawings) and/or all the steps of the described method can be combined in any combination, with the exception of combinations of such mutually exclusive features and/or steps.

BRIEF DESCRIPTION OF THE DRAWINGS

To better understand the invention, its objects and advantages, the following figures are attached to the specification in which the following is depicted.

PREFERRED EMBODIMENTS OF THE INVENTION

FIGS. 1, 5, 6 and 8 show flowcharts of the method for monitoring a structure according to preferred embodiments of the invention.

The method will be described as applied for monitoring an aircraft, although it is applicable to other structures, such as a bridge or a ship. Depending on the structure to be monitored different operational parameters will be used, namely those parameters known to have an influence on the strain of said structure.

Figure 1:
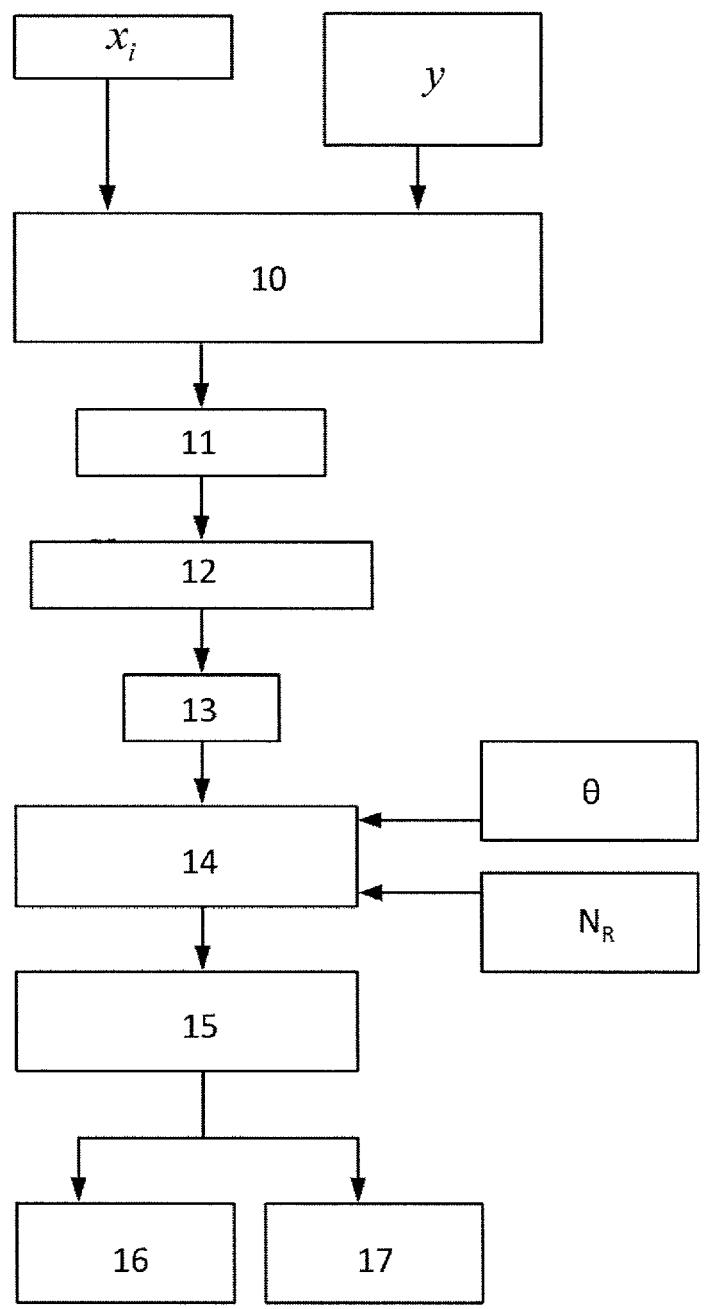
FIG. 1 shows a flow diagram according to a preferred embodiment of the data redundancy elimination step of the method of the invention.

The method starts with a dataset comprising a group of parameter signals data $x_i$ and strain signals data y from a flight or a group of flights recorded synchronously (FIG. 1). This dataset is acquired and downloaded to the processing facility. In the processing facility the dataset is pre-processed comprising the following steps: error detection and correction, filtering and re-sampling, thus obtaining the so-called low frequency dataset (FIGS. 5, 22), composed of all corrected signals with the same sampling rate and bandwidth.

The dataset acquired for times $t_1, t_2, \ldots t_m$ can be understood as a multidimensional dataset, $$M = \begin{bmatrix} x_1(t_1) & x_1(t_2) & \cdots & x_1(t_{m-1}) & x_1(t_m) \\ x_2(t_1) & x_2(t_2) & & x_2(t_{m-1}) & x_2(t_m) \\ \vdots & & \ddots & & \vdots \\ x_n(t_1) & x_n(t_2) & \cdots & x_n(t_{m-1}) & x_n(t_m) \\ y(t_1) & y(t_2) & & y(t_{m-1}) & y(t_m) \end{bmatrix} =$$

$$[\bar{\mu}_1 \cdots \bar{\mu}_m] \to \bar{\mu}_j = \begin{bmatrix} x_1(t_j) \\ x_2(t_j) \\ \vdots \\ x_n(t_j) \\ y(t_j) \end{bmatrix}$$

where the strain signal y and the parameters signals $x_i$ are related by means of a functional relationship, the parameters signals $x_i$ being the independent variables and the strain signal y being the dependent variable of the functional relationship:

$$y(t_j) = f(x_1(t_j), x_2(t_j), \ldots, x_n(t_j))$$

A purpose of the method is to delete dataset redundancy, if existing, in order to use the minimum amount of data to fit a model with them. Thus, the data is considered as recordings of $\bar{\mu}_j = \bar{\mu}(t_j)$ vectors to be compared with.

The pre-processed dataset with parameters $x_i$ and strain signals y is fed into a selector (10) that associates for every calculation point $t_j$ the parameter signals $x_i$ that have a functional relationship with each corresponding strain signal y. For every calculation point $t_j$, the data are vectorized (11) and the vectorized data $\bar{\mu}_j$ are normalized and their modulus evaluated (12).

Preferably, in the normalization of the pre-processing step, the maximum and minimum values for $x_i$ and y are determined in order to convert the physical parameters range into a normalized range [−1,1]:

$$\begin{bmatrix} x_1^{min} & x_1^{max} \\ x_2^{min} & x_2^{max} \\ \vdots & \vdots \\ y^{min} & y^{max} \end{bmatrix} \tilde{x}_i^j = \tilde{x}_i(t_j) = 2 \cdot \frac{x_i(t_j) - x_i^{min}}{x_i^{max} - x_i^{min}} - 1;$$

$$i = 1, \ldots, n, j = 1, \ldots, m;$$

$$\tilde{y}^j = \tilde{y}(t_j) = 2 \cdot \frac{y(t_j) - y^{min}}{y^{max} - y^{min}} - 1; j = 1, \ldots, m;$$

The modulus $\|\bar{\mu}_j\| = \|\bar{\mu}(t_j)\|$ being determined as:

$$\|\bar{\mu}_j\| = \|\bar{\mu}(t_j)\| = \sqrt{\sum_{i=1}^{n} \tilde{x}_i(t_j)^2 + \tilde{y}(t_j)^2}$$

Figure 2:
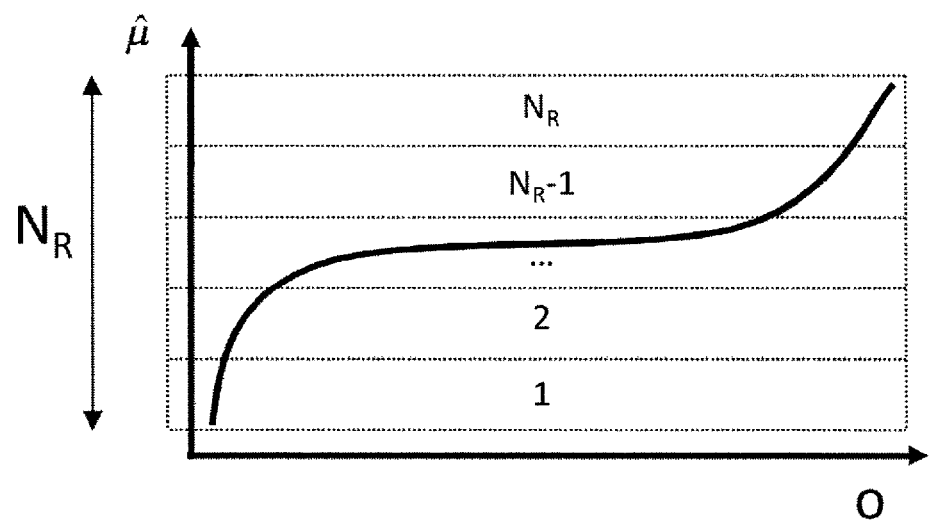
FIG. 2 shows the process of sorting high redundant datasets.

In a subsequent step the vectorized data $\|\bar{\mu}_j\|$ are sorted (13) $\hat{\mu}_j = \mu(o_j)$ according to their modulus values from minimum value to maximum value. The statistical distribution of high redundant datasets when ordered by modulus is typically represented by a distribution as shown in FIG. 2. In this distribution 10 three zones can be distinguished:

(1) A first zone of low modulus and high variation,
(2) a second zone of medium modulus and low variation, and
(3) a third zone of high modulus and high variation.

In order to reduce the number of data by neglecting redundant data, redundancy is evaluated (14) using two predefined parameters: the correlation multi-dimensional distance between two data vectors (θ), for angle comparison, and the number of calculation groups ($N_R$), for modulus comparison.

Figure 3:
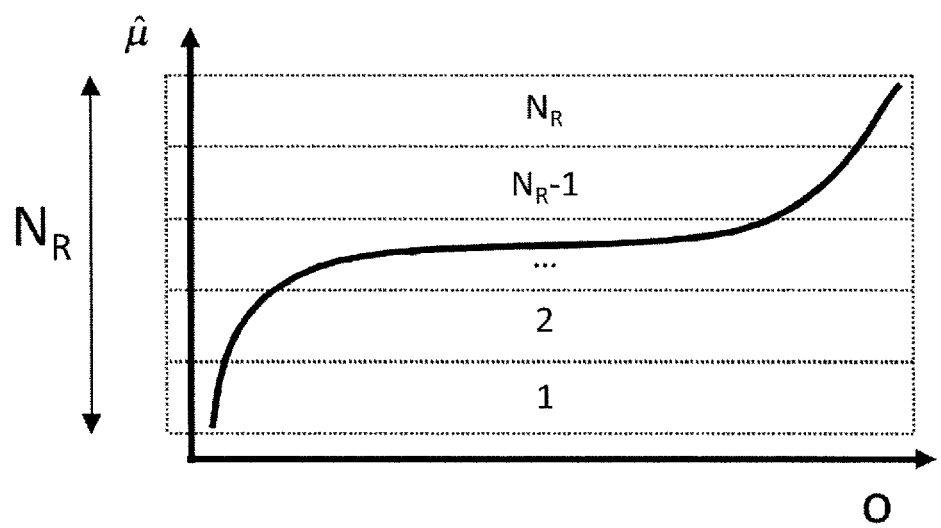
FIG. 3 shows division of sorted data into groups with similar modulus.

Dividing then the data in $N_R$ groups having similar values of modulus can be viewed as a first filtering to compare data vectors (FIG. 3), all the data vectors included in a group having a modulus within a established range. The number of vectors falling within each group depends on the zone of the statistical distribution: In the first and third zones of FIG. 2 there are few vectors in each group, due to the high modulus variation, whereas in the second zone there are many vectors, due to the low modulus variation in this zone.

For each group, the angle between vectors is computed in order to delete vectors with similar modulus and small angles. Inside the group, two vectors $\bar{\bar{\mu}}^1, \bar{\bar{\mu}}^2$ are considered:

$$\tilde{\mu}^1 = \begin{bmatrix} \tilde{x}_1^1 \\ \tilde{x}_2^1 \\ \vdots \\ \tilde{y}^1 \end{bmatrix}, \tilde{\mu}^2 = \begin{bmatrix} \tilde{x}_1^2 \\ \tilde{x}_2^2 \\ \vdots \\ \tilde{y}^2 \end{bmatrix}$$

and the angle $\alpha_{1\rightarrow 2}$ between them is determined:

$$\frac{\tilde{\mu}^2 \cdot \tilde{\mu}^1}{\|\tilde{\mu}^1\| \cdot \|\tilde{\mu}^2\|} = \cos(\alpha_{1\rightarrow 2})$$

If $\cos(\alpha_{1\rightarrow 2}) \leq \sqrt{1-\sin^2(\theta)}$ one of the two vectors can be deleted because both have similar modulus (since they are contained in the same modulus group) and they define a small angle (i.e. less than the predefined angle $\theta$).

If this operation is performed for every pair of vectors within each group, only the significant points for each group will be retained, all the redundant data being deleted. The result of the redundancy evaluation is a set of positions of significant points in the M dataset (15) according to the predefined parameters $(\theta, N_R)$. With this information the recorded and pre-processed dataset, M, can then be divided into a training dataset (16), composed of the significant points, and a validation dataset (17) that contains the redundant information.

Figure 7A:
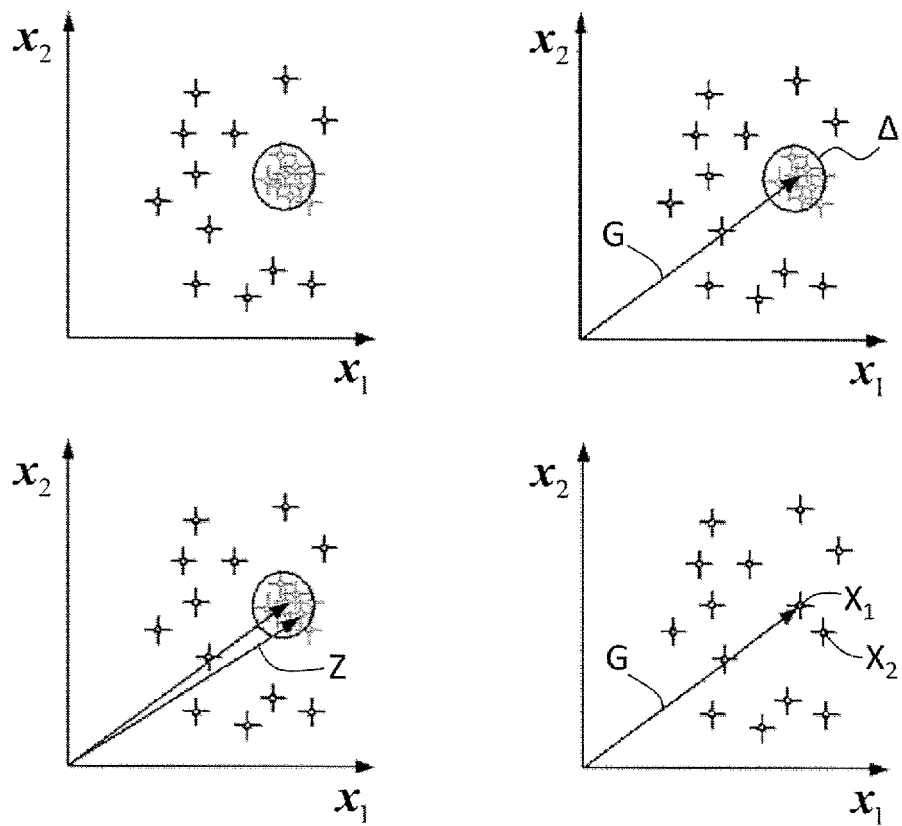
FIG. 7 (A and B) shows two graphical examples illustrating the data reduction process for deletion of redundant data.

FIG. 7 shows two examples of the construction of the significant point dataset. In FIG. 7A a two-dimensional dataset with a region having a high density of points is shown. In this example, variables $x_1, x_2$ could be two flight parameters, respectively the Mach number and the vertical load factor. The centre of gravity (G) of the region having a high density of points is taken with a certain precision circle $\Delta$, so it can be considered that every point Z inside this circle is represented by a significant point located in the centre of gravity (G) with a certain precision denoted by the depicted circle. This precision is proper to consider that if a model is fitted with the significant point G it could interpolate the points inside the circle with a determined precision, so it represents the circle area with the significant point $X_1$ and delete the rest points within the circle. Points outside the circle area, such as $X_2$ are kept. The significant point $X_1$ thus acquires statistical meaning in terms of a distribution according to the points it represents.

Figure 7B:
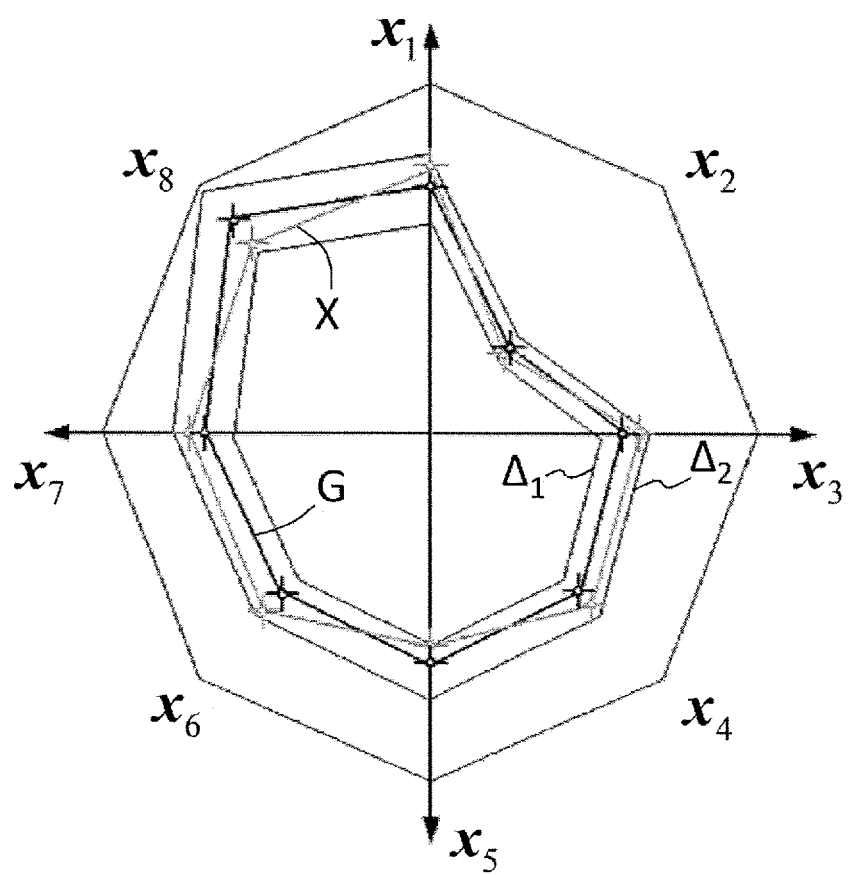

FIG. 7B shows the multidimensional interpretation of the previous example in terms of a wind rose, in which each course represents a variable, e.g. the Mach number, the altitude, vertical load factor, engine thrust, the aileron position, the elevator position, the gross weight and the center of gravity. In this multidimensional representation every point X is represented by a polygon, and the polygon crown $\Delta_1$-$\Delta_2$ around a significant point G corresponds to the circle of the previous two-dimensional representation. Thus, every polygon X contained in this crown is represented by its significant point G, which acquires the statistical meaning of a multidimensional distribution.

The acquisition of parametric $x_i$ data may be performed by an on-board recorder that acquires the appropriate flight parameters from other aircraft computers and/or by dedicated sensors. The connections between sensors and recorder can be made by means of standardized data buses and digital transmission protocols such as ARINC429, MIL1553B, RS232, etc., so the recorder will preferably have the corresponding acquisition interfaces for all of those data formats. The parametric data have to be recorded synchronously. Parametric data can be extracted for example from aircraft existing computers, engines control units, landing gear brakes and steer, flight control, air data, inertial data, weight and balance or central management. Examples of parametric data can be speed, altitude, vertical load factor, Mach number, etc.

Additionally, strain data y is acquired by at least one physical strain sensor installed in a subset of the fleet, preferably in a representative aircraft of each of the different structural configurations of the fleet. The strain sensors are connected to the recorder analogically, forcing it to have all the necessary acquisition elements of the particular strain sensor used, or digitally, getting the data from other equipment, forcing the recorder to be compatible with the transmission protocol of the data of this intermediate item and to maintain the synchronization with the aircraft parameters.

The main purpose of the method is to build the functional relationship between strain measured at one or more than one points of the structure, y (dependent variable), and the operation parameters, $x_i$ (independent variables, such as speed, altitude, vertical load factor, etc). This functional relationship can be modelled with a non-adaptive prediction functional supervised approximation method, such as an ANN, if some conditions are satisfied. Although reference will be made to an ANN, it will be understood that any other non-adaptive prediction functional supervised approximation method can be used.

Figure 4:
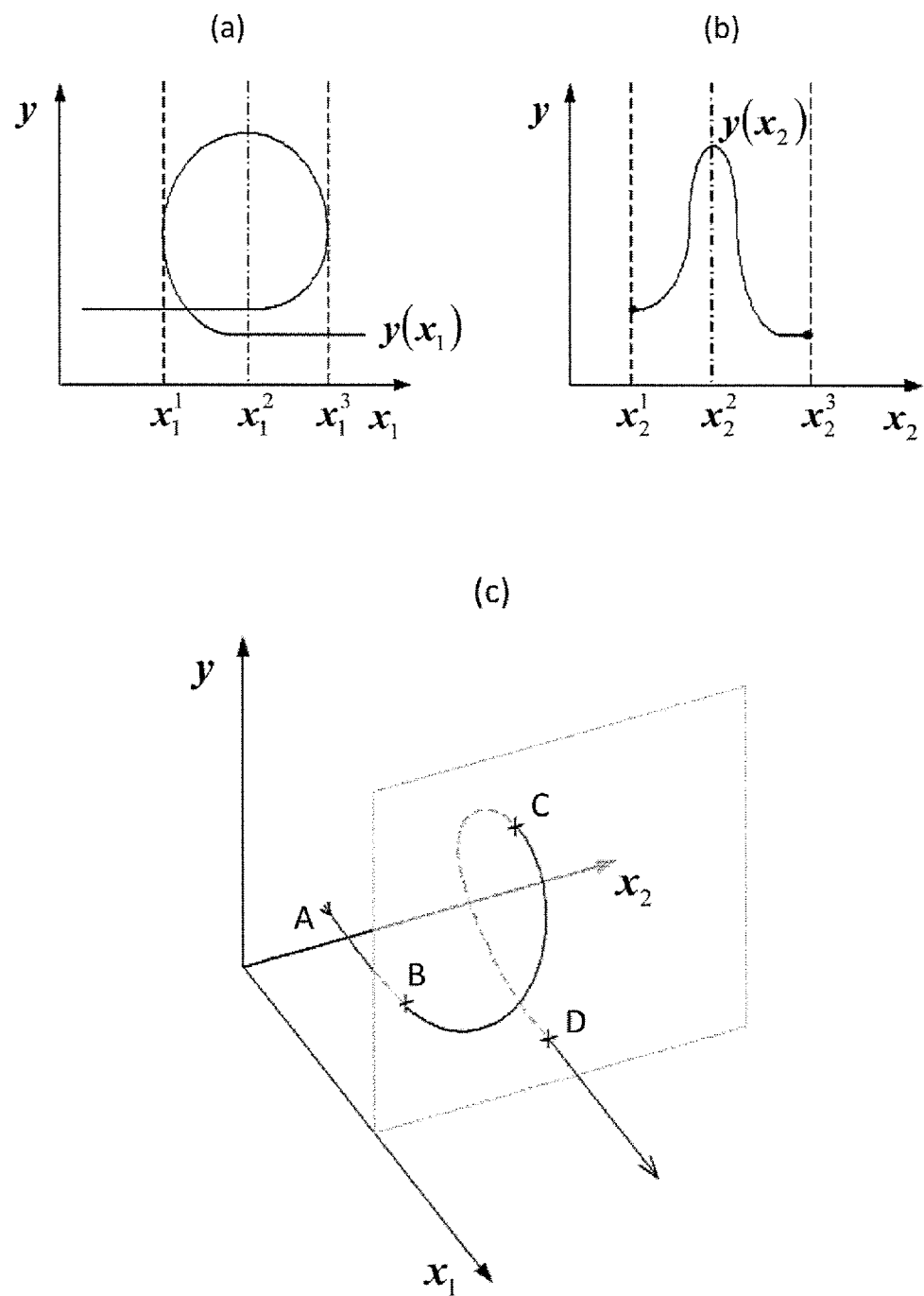
FIG. 4 shows an example of single-valued autonomous function (time independent) to clarify the relationships between parameters and structure strain to be modelled.

First, the functional relationship has to be uni-evaluated, i.e. for each combination of operation parameters must exist one and only one strain value. FIG. 4 explains this with an example. Let's assume that it is desired to approximate the strain at some location of the structure during a flight by using only one operation parameter $x_1$ (for example, the Mach number (FIG. 4(a)). In this example the functional relationship is not uni-evaluated between Mach values $x_1^1$ and $x_1^3$, because for each Mach value up to three strain values can be found. Consequently, in this case there is not a unique functional relationship in this interval. However, if a second parameter $x_2$ not multi-evaluated in its operation range respect to the strain is added to the functional relationship (for example, the altitude (FIG. 4(b)), the global relationship between altitude—mach and Strain becomes uni-evaluated (FIG. 4(c)). Thus, the introduction of enough variables to the functional relationship enables its approximation with an artificial neural network inside the operational ranges of parameters (point A to D in FIG. 4(c)).

In addition, the functional relationship has to be autonomous, time-independent. All of the strain values have to depend on the operation parameters and never on the time sample.

Finally, the sampling rate and the bandwidth of the data, parameters and strain, used to fit the model must be the same.

To fulfil these three conditions, each strain measurement point of the structure must have a group of fundamental parameters that have more impact on the relationship than others. The parameters influence can be grouped by structural zones. As an example, one of the most important parameters in the wing root of an aircraft is the vertical load factor measured at the center of gravity, while in some parts of the fuselage dominant loading is caused by the cabin differential pressure, so these parameters are the reference when determining the strains in those structural elements.

Consequently, the relationship between parametric data and strain is modelled using an Artificial Neural Network, and trained using the significant points dataset.

Figure 5:
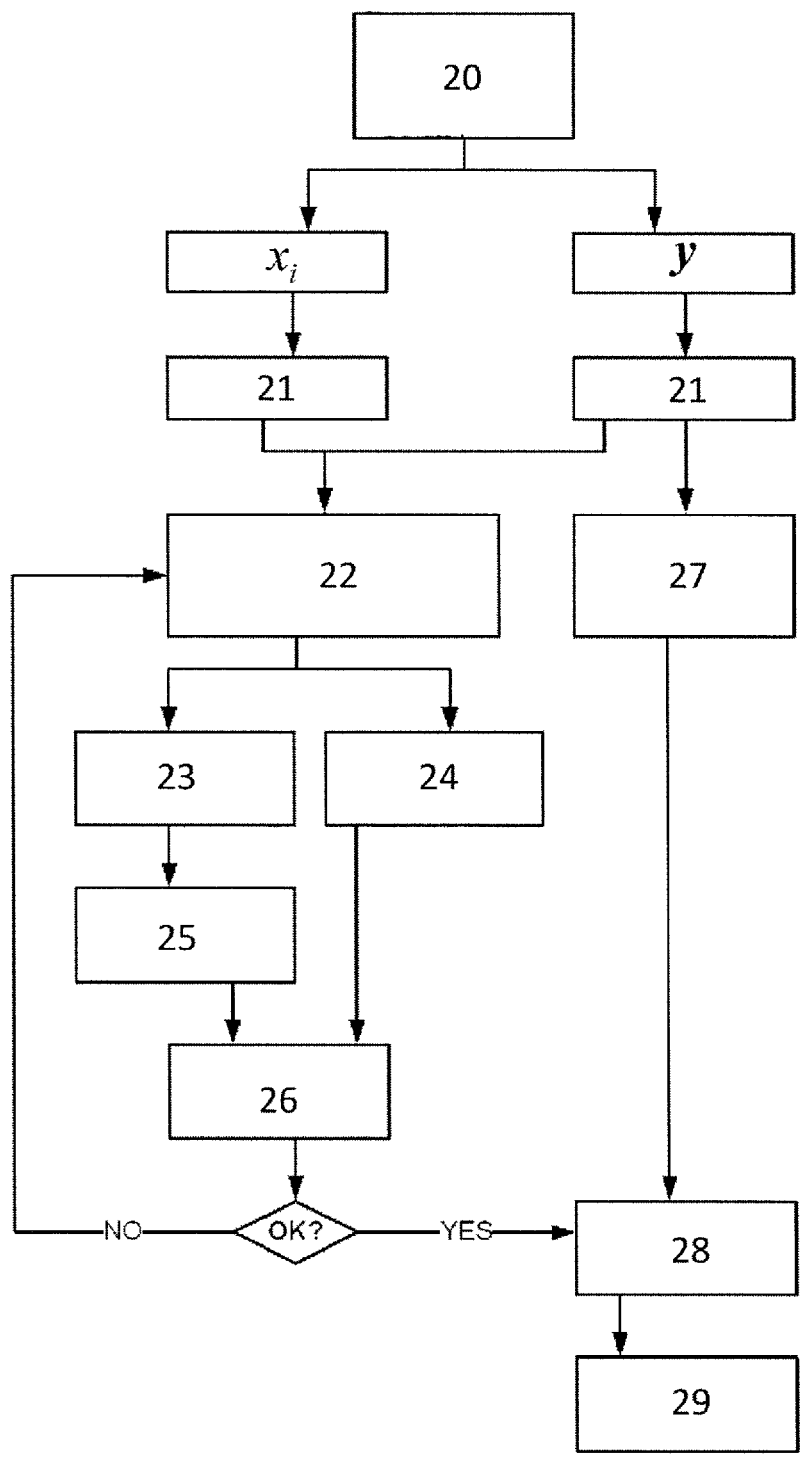
FIG. 5 shows the flow diagram of a preferred embodiment of the method of the invention.

FIG. 5 shows the process used to fit the models. The starting point of the process is the data acquisition by the on-board recorder for those aircraft with strain gauges installed, generating datasets with operation parameters $x_i$ and strain gauges signals v. Then, the operation parameters $x_i$ relevant for each strain measurement point (along with the strain y itself) are extracted from this dataset (20) and a subset {$x_i$, y} is built. This subset {$x_i$,y} is pre-processed (21), preferably including processing such as error detection and correction, signals synchronization (i.e. elimination of delays), signals filtering to match different bandwidths and to split high (27) and low frequency (22) datasets, and signals re-sampling to match different sampling rates. The low frequency dataset (22) contains parameters $x_i$ and strains y with the same bandwidth and sampling rate and will be used for Artificial Neural Network fitting (25), while the high frequency dataset (27) contains the full bandwidth strain data, and will be used to calculate the Adjustment Factors (28).

The low frequency dataset is then introduced in the flow of the data reduction 25 algorithm flowchart (22) obtaining the training dataset (23), significant points of the low frequency dataset to fit the Artificial Neural Network and the validation dataset (24), redundant information of the low frequency dataset. Usually the ratio between significant and not significant points can be 100 to 1, which makes the training of the Artificial Neural Network approachable. The training dataset (23) is used to train the Artificial Neural Network model (25). Feeding the trained Artificial Neural Network (25) with redundant dataset (24) the model can be validated (26). If the validation error is similar to the training error, the process can continue and the adjustment factors are computed (28); if not, the training data and/or the models have to be modified. With the trained and validated Artificial Neural Network model and the full bandwidth strain dataset (27) the adjustment factors (AF) are obtained (28). The method to obtain the Adjustment Factor (AF) comprises the evaluation of the ratio between fatigue life computed from full bandwidth strain time series and fatigue life computed from simulated strain time series coming from the Artificial Neural Networks models. Therefore, the Adjustment Factors (AF) represent the ratio between the Artificial Neural Network model output (low frequency calculated strain) and the full bandwidth strain in terms of fatigue damage. And it will be applied to the virtual sensors output fatigue calculations to compensate high frequency and model performance effects. Finally, the adjustment factors are included in the artificial neural network model (29) in order to complete it. The final set of Artificial Neural Network and AF is then ready to be implemented in a subsequent step of damage calculation.

Figure 6:
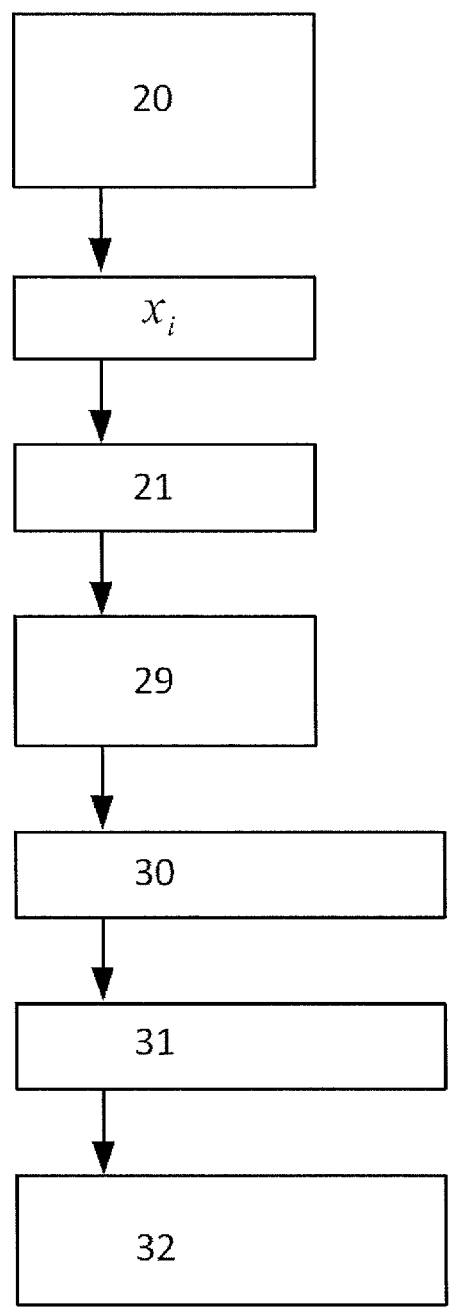
FIG. 6 shows the flow diagram of an embodiment of the method of the invention comprising fatigue life prognosis and crack growth calculation using stress time series coming from ANN—based virtual strain sensors.

FIG. 6 describes the operation of a preferred embodiment of the method of the invention, comprising a step of calculation of fatigue damage accrual in a particular location. The data (20) comprising the parametric data $x_i$ is downloaded from the recorder and pre-processed (21) (including error detection and correction, synchronization, filtering and re-sampling). The trained and validated Artificial Neural Network model (29) including the appropriate Adjustment Factors (to be applied later) is fed with pre-processed data to obtain the computed strain values time history (30). With the calculated stress time histories (31) the fatigue and crack growth analysis is performed (32) at the selected location or its vicinity, and the Adjustment Factor for the location is applied to evaluate the real fatigue life consumption and/or crack growth. This process can be applied to all the selected stress locations of every aircraft of the fleet.

Figure 8:
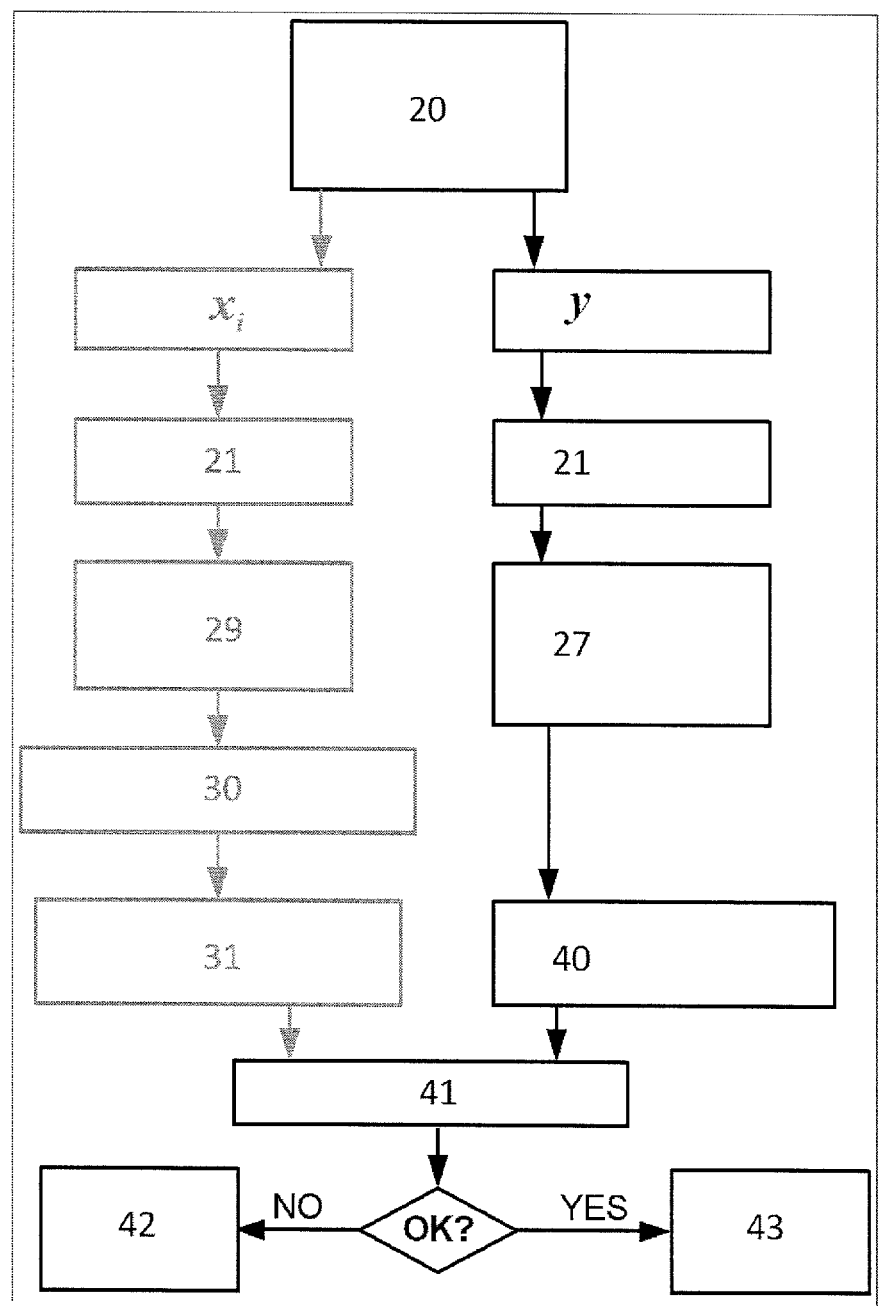
FIG. 8 shows the flow diagram of a preferred embodiment of the method comprising in-service continuous system self-validation.

FIG. 8 shows an embodiment of the method of the invention comprising the step of Artificial Neural Network based models continuous performance (also called continuous self-validation), which is applicable to the aircraft of the fleet in which physical strain sensors have been installed.

The left hand flowchart (in gray), is essentially the same as in FIG. 6, the in service workflow of the system. The right hand part of the flowchart (depicted in black) comprises the system self-validation. The acquired data (20) containing parametric data $x_i$ and strain data y are downloaded to extract the strain sensor signals y, which are pre-processed (21) including error detection and correction and filtering. The pre-processed output is the full bandwidth strain data (27), which is used to obtain real stress time history (40). The real strain time series (40) thus obtained from strain measurement is compared (41) with the calculated strain time series (31) computed with the Artificial Neural Network model and corrected with the Adjustment factors (this comparison can be made in terms of time series, stress spectra from rainflow analysis, fatigue life, etc). The result of this comparison (41) is checked to determine whether it is within a predefined margin or not. If the result of this comparison (41) falls within the predefined margin, the artificial neural network based models are considered valid (43). If not, the artificial neural network based models must be updated (42) following the procedure of model calculation.

The invention claimed is:

1. A method of monitoring a structure, comprising:
  a) utilizing an acquisition and recording device and at least one strain sensor to acquire data, the data comprising a plurality of operational parameters $x_i(t_j)$ and at least one strain data $y(t_j)$, the operational parameters $x_i$ and the strain data y being acquired synchronously over a time series basis $(t_1, t_2, \ldots, t_m)$ using the same or different sampling rates;
  b) building a significant points dataset from the data acquired in a) using a processor; and
  c) modelling, in the processor, a relationship between the operational parameters $x_i(t_j)$ and the strain data $y(t_j)$ using the built significant points dataset to train a non-adaptive prediction functional supervised approximation method,
wherein building a significant points dataset comprises:
  (b1) for each time sample $t_j$, j=1, ..., m, determining the data modulus $\|\bar{\mu}(t_j)\|$ of data vectors $\bar{\mu}(t_j)$ defined as:

$$\bar{\mu}(t_j) = (x_1(t_j), x_2(t_j), \ldots, x_n(t_j); y(t_j)),$$

the data modulus $\|\bar{\mu}(t_j)\|$ being calculated as:

$$\|\bar{\mu}(t_j)\| = \sqrt{\sum_{i=1}^{n} \tilde{x}_i(t_j)^2 + \tilde{y}(t_j)^2}$$

with $$\tilde{x}_i(t_j) = 2 \cdot \frac{x_i(t_j) - x_i^{min}}{x_i^{max} - x_i^{min}} - 1, \text{ for } i = 1, \ldots, n;$$

$$\tilde{y}(t_j) = 2 \cdot \frac{y(t_j) - y^{min}}{y^{max} - y^{min}} - 1$$

and $x_i^{min}$, $x_i^{max}$, $y^{min}$, $y^{max}$ being respectively the minimum and maximum values for $x_i$ and the minimum and maximum values for y in the time series $(t_1, t_2, \ldots, t_m)$;

(b2) sorting the data vectors $\bar{\mu}(t_j)$, j=1, ..., m, in $N_R$ groups according to the value of their modulus, each group including data with values of modulus within a defined range;

(b3) computing within each group the angle α between pairs of vectors and when the angle between a first vector and a second vector is less than or equal to a predetermined angle θ, deleting one of the two vectors.

2. The method according to claim 1, wherein in (b3) the data vectors $\bar{\mu}(t_j)$ having maximum and minimum strain values are retained in each group.

3. The method according to claim 1, wherein a minimum number of group points is associated to each group, such that when the number of significant points retained in a group after (b3) is below the minimum number, the group is split into two groups of equal size and (b3) is repeated until the minimum number of significant points is retained in the original group.

4. The method according to claim 1, comprising pre-processing the acquired data ($x_i$, y) prior to building the significant points dataset, and wherein pre-processing the acquired data preferably includes at least application of an error detection and correction algorithm, normalization, filtering, re-sampling and/or generating a low frequency dataset.

5. The method according to claim 4, wherein pre-processing the acquired data ($x_i$, y) comprises generating a low frequency dataset and the significant points dataset are built from the low frequency dataset.

6. The method according to claim 1, comprising validating the relationship modelled between the operational parameters $x_i(t_j)$ and the strain data $y(t_j)$ using the acquired data which are not included in the significant points dataset and optionally points taken from the significant points dataset.

7. The method according to claim 6, comprising:
pre-processing the acquired data ($x_i$, y) prior to building the significant points dataset, and wherein pre-processing the acquired data ($x_i$, y) comprises generating a low frequency dataset, wherein the significant points dataset are built from the low frequency dataset; and
feeding the trained and validated modelled relationship with the original, not-reduced, low frequency dataset, and computing adjustment factors as the ratio between the model output obtained in the previous step, i.e. the low frequency calculated strain, and the full bandwidth strain.

8. The method according to claim 7, comprising computing a strain history of at least one structure based on the trained and validated model, the acquired operational parameters and the computed adjustment factors, the acquired parameters being optionally pre-processed.

9. The method according to claim 8, comprising computing corrected strains using the adjustment factors.

10. The method according to claim 9, wherein the acquired parameters are pre-processed, and wherein pre-processing comprises producing the original bandwidth strain, the method further comprising checking the in-service continuous system performance, by comparing the full bandwidth strain with the computed strain.

11. The method according to claim 9, comprising using the computed strains to calculate fatigue life and damage tolerance consumption of at least one structure.

12. The method according to claim 1, wherein the non-adaptive prediction functional supervised approximation method is performed by an ANN.

13. The method according to claim 1 applied to an aircraft structure, wherein the operational parameters $x_i(t_j)$ are obtained from a number N of aircraft and the strain data $y(t_j)$ are obtained from a number M of reference aircraft, M being less or equal than N, and preferably M being substantially 10-20% of N.

14. A system for monitoring a structure comprising:
an acquisition and recording device adapted to collect operational parameters from at least one structure, at least one physical strain sensor installed in a selected location of the structure, and a processor,
wherein the system for monitoring the structure is adapted to: acquire data, the data comprising a plurality of operational parameters $x_i(t_j)$ and at least one strain data $y(t_j)$, the operational parameters $x_i$ and the strain data y being acquired synchronously over a time series basis ($t_1$, $t_2$, ..., $t_m$) using the same or different sampling rates;
build a significant points dataset from the data acquired; and
model a relationship between the operational parameters $x_i(t_j)$ and the strain data $y(t_j)$ using the built significant points dataset to train a non-adaptive prediction functional supervised approximation method,
wherein building a significant points dataset comprises:
for each time sample $t_j$, j=1, ..., m, determining the data modulus $\|\bar{\mu}(t_j)\|$ of data vectors $\bar{\mu}(t_j)$ defined as:

$$\bar{\mu}=(t_j)=x_1(t_j),x_2(t_j),\ldots,x_n(t_j);y(t_j)),$$

the data modulus $\|\bar{\mu}(t_j)\|$ being calculated as:

$$\|\bar{\mu}(t_j)\| = \sqrt{\sum_{i=1}^{n}\tilde{x}_i(t_j)^2 + \tilde{y}(t_j)^2}$$

with $$\tilde{x}_i(t_j) = 2\cdot\frac{x_i(t_j) - x_i^{min}}{x_i^{max} - x_i^{min}} - 1, \text{ for } i = 1, \ldots, n;$$

$$\tilde{y}(t_j) = 2\cdot\frac{y(t_j) - y^{min}}{y^{max} - y^{min}} - 1$$

and $x_i^{min}$, $x_i^{max}$, $y^{min}$, $y^{max}$ being respectively the minimum and maximum values for $x_i$ and the minimum and maximum values for y in the time series ($t_1$, $t_2$, ..., $t_m$);
sorting the data vectors $\bar{\mu}(t_j)$, j=1, ..., m, in $N_R$ groups according to the value of their modulus, each group including data with values of modulus within a defined range; and
computing within each group the angle α between pairs of vectors and when the angle between a first vector and a second vector is less than or equal to a predetermined angle θ, deleting one of the two vectors.

15. A system for monitoring a structure according to claim 14, wherein the structure is an aircraft, the acquisition and recording device is adapted to collect aircraft operational parameters from the aircraft and the at least one physical strain sensor is installed in a selected location of the aircraft structure.

* * * * *